United States Patent
Huq

(10) Patent No.: US 11,072,028 B2
(45) Date of Patent: Jul. 27, 2021

(54) OIL-LESS PNEUMATIC MOTOR HAVING GRAPHITE VANES FORMED WITH BEVELED EDGES, OFF-STANDING FLANGES, AND ROUNDED CORNERS

(71) Applicant: Medtronic PS Medical, Inc., Fort Worth, TX (US)

(72) Inventor: Md Zahedul Huq, Keller, TX (US)

(73) Assignee: Medtronic PS Medical, Inc., Fort Worth, TX (US)

( * ) Notice: Subject to any disclaimer, the term of this patent is extended or adjusted under 35 U.S.C. 154(b) by 368 days.

(21) Appl. No.: 15/907,583

(22) Filed: Feb. 28, 2018

(65) Prior Publication Data
US 2019/0262909 A1    Aug. 29, 2019

(51) Int. Cl.
| B23B 45/04 | (2006.01) |
| A61B 17/16 | (2006.01) |
| F01C 13/02 | (2006.01) |
| A61B 17/00 | (2006.01) |
| F01C 1/344 | (2006.01) |

(52) U.S. Cl.
CPC ........ *B23B 45/044* (2013.01); *A61B 17/1624* (2013.01); *A61B 17/1628* (2013.01); *F01C 1/3441* (2013.01); *A61B 2017/00544* (2013.01); *A61B 2017/00845* (2013.01); *B23B 2270/027* (2013.01); *F01C 13/02* (2013.01)

(58) Field of Classification Search
CPC ............ A61B 17/1624; A61B 17/1628; A61B 2017/00544; A61B 2017/00845; B23B 2270/027; B23B 45/044; F01C 13/02; F01C 1/3441; F01C 1/344; F01C 18/344; F01C 29/0042; F01C 2210/1005; F01C 2270/16; F04C 18/344; F04C 29/0042; F04C 2210/1005; F04C 2270/16
USPC ................. 418/152, 178, 70, 179, 225, 270; 173/168, 177, 218, 164, 170, 171
See application file for complete search history.

(56) References Cited

U.S. PATENT DOCUMENTS

| 1,444,269 A | * | 2/1923 | Piatt ........................ F04C 2/352 |
| | | | 418/46 |
| 2,833,465 A | * | 5/1958 | Cable .................... F04C 2/3441 |
| | | | 418/236 |
| 3,254,606 A | * | 6/1966 | Rosaen ............... F01C 21/0863 |
| | | | 418/80 |

(Continued)

FOREIGN PATENT DOCUMENTS

JP         2016173052 A   *   9/2016

OTHER PUBLICATIONS

Derwent English Abstractor JP2016173052A (Year: 2016).*

(Continued)

*Primary Examiner* — Mary Davis
*Assistant Examiner* — Paul W Thiede
(74) *Attorney, Agent, or Firm* — Harness, Dickey & Pierce, P.L.C.

(57) ABSTRACT

The pneumatic drill has member defining an air input and an air output and a housing defining an internal cylindrical chamber having bearing surfaces having a through axis. A driven shaft is coupled to the tool engaging chuck that defines a plurality of longitudinal slots. The driven shaft is disposed within the chamber and has a longitudinal axis offset from the through axis. A plurality of vanes each being partially formed of graphite that are individually disposed within one of the plurality's of longitudinal slots. Two of the vanes, the housing, and the driven shaft define a moving compression chamber.

18 Claims, 7 Drawing Sheets

(56) References Cited

U.S. PATENT DOCUMENTS

| | | | | |
|---|---|---|---|---|
| 3,734,652 | A * | 5/1973 | Barnett | F01C 13/02 |
| | | | | 418/70 |
| 4,804,317 | A | 2/1989 | Smart et al. | |
| 4,955,985 | A * | 9/1990 | Sakamaki | F01C 21/0809 |
| | | | | 418/257 |
| 5,653,398 | A * | 8/1997 | Fohl | F01C 21/0863 |
| | | | | 242/374 |
| 5,782,836 | A * | 7/1998 | Umber | A61B 17/32002 |
| | | | | 606/79 |
| 6,270,345 | B1 | 8/2001 | Abbott et al. | |
| 7,222,680 | B2 * | 5/2007 | Livingston | B25F 5/00 |
| | | | | 173/168 |
| 7,621,730 | B2 * | 11/2009 | Del Rio | A61B 17/1624 |
| | | | | 418/270 |
| 8,556,922 | B2 * | 10/2013 | Tidwell | A61B 17/1628 |
| | | | | 606/167 |
| 2002/0141894 | A1 * | 10/2002 | Kirtley | F01C 21/0809 |
| | | | | 418/152 |
| 2006/0089623 | A1 * | 4/2006 | Tidwell | A61B 17/1628 |
| | | | | 606/1 |
| 2008/0122302 | A1 * | 5/2008 | Leininger | B25F 5/021 |
| | | | | 310/50 |
| 2008/0208229 | A1 * | 8/2008 | Tidwell | A61B 17/1628 |
| | | | | 606/167 |
| 2012/0306206 | A1 * | 12/2012 | Agrawal | F01D 15/10 |
| | | | | 290/52 |
| 2013/0183171 | A1 * | 7/2013 | Hwang | F04C 2/3446 |
| | | | | 417/356 |
| 2017/0002117 | A1 * | 1/2017 | Layman | B29B 17/02 |
| 2017/0298986 | A1 * | 10/2017 | Ito | F16C 33/10 |

OTHER PUBLICATIONS

English Machine Translation of JP2016173052A. Translated from Espacenet on Oct. 27, 2020. (Year: 2016).*

International Search Report and Written Opinion dated Jun. 3, 2019 in corresponding/related International Application No. PCT/US2019/019821.

International Preliminary Report on Patentability dated Sep. 10, 2020 in corresponding International Application No. PCT/US2019/019821.

* cited by examiner

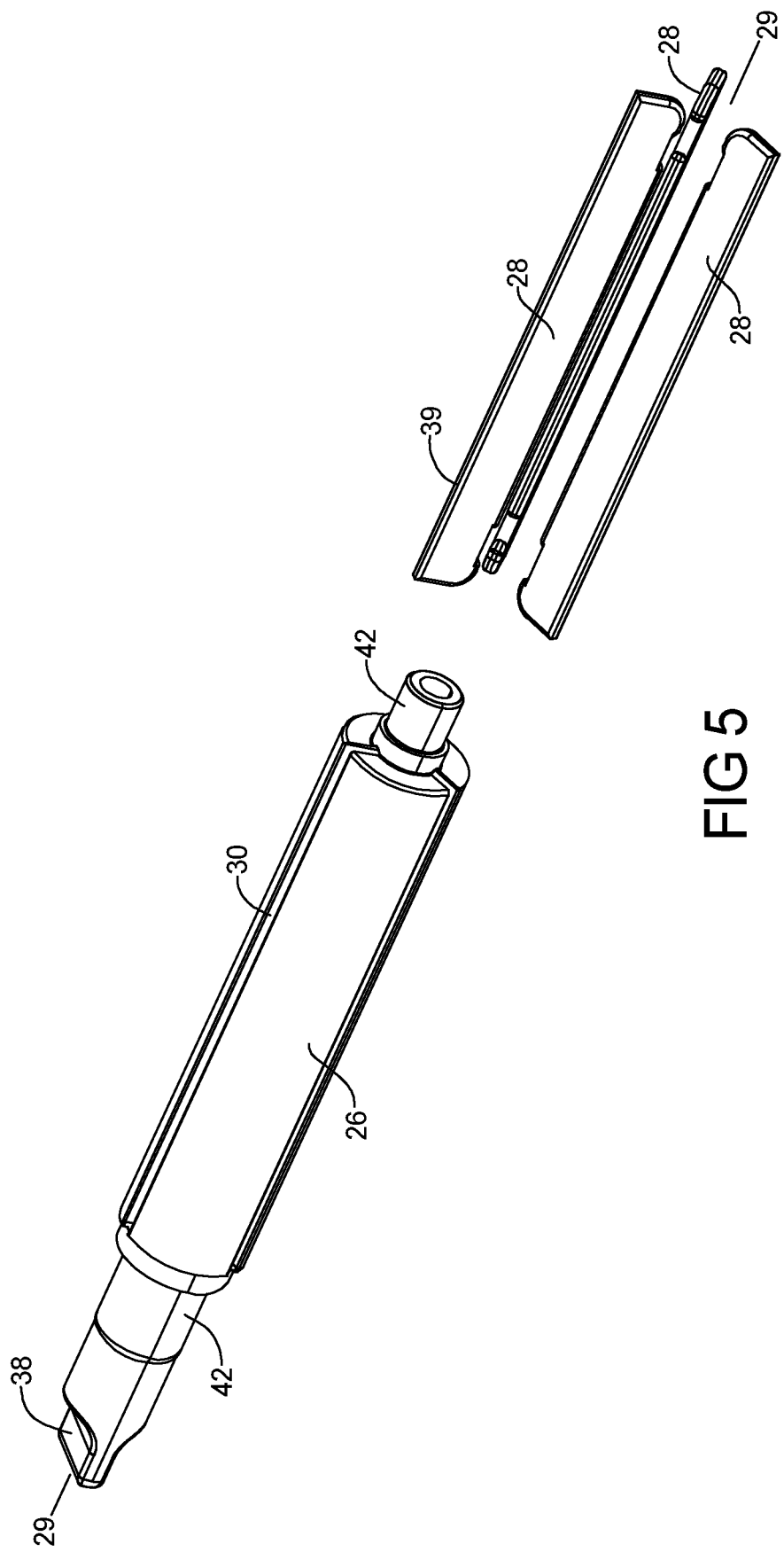

OIL-LESS PNEUMATIC MOTOR HAVING GRAPHITE VANES FORMED WITH BEVELED EDGES, OFF-STANDING FLANGES, AND ROUNDED CORNERS

FIELD

The present disclosure relates to a pneumatic drill and more particularly to an oil-less pneumatic motor for a drill having graphite vane members.

BACKGROUND

This section provides background information related to the present disclosure that is not necessarily prior art.

In today's surgical environment often utilizes high-speed pneumatic drills to cut tissue such as bone. These high-speed drills, while very small and effective, utilize cutting instruments, that rotate at several tens of thousands of RPM. To reduce the amount of friction induced heat and wear within these systems and to reduce the drill size, the drills often utilize liquid lubricants that are often fed into the feed airstream. The metering of the lubricant often leads to costs and complications related drill life and use conditions and ease of drill system management. It is therefore an object of the invention to overcome these complications.

SUMMARY

This section provides a general summary of the disclosure, and is not a comprehensive disclosure of its full scope or all of its features.

According the present teaching, a pneumatic drill is provided having a tool engaging chuck, and a pneumatic motor. The pneumatic motor has a housing defining an air input and an air output and further defining an internal cylindrical chamber having bearing surfaces with a through axis. A driven shaft is coupled to the tool engaging chuck. The shaft defines a plurality of longitudinal slots which are configured to slidably accept longitudinal vanes. The driven shaft is disposed within the cylindrical chamber and has a longitudinal axis offset from the through axis. The plurality of polymer containing vanes containing graphite are individually disposed within one of the plurality of longitudinal slots. According to an alternate teaching, two of the vanes, the housing, and the driven shaft define a moving compression chamber.

According to an alternate teaching, the vane is slidably disposed within the slot, and slidably engaged against the housing bearing surface.

According to an alternate teaching, the vane has a laminar composite structure and includes graphite particles disposed in a Polyether Ether Ketone (PEEK) matrix.

According to an alternate teaching, a pneumatic drill is provided having a tool engaging chuck, and a pneumatic motor. The pneumatic motor has a housing defining an air input and an air output and further defining an internal cylindrical chamber having bearing surfaces. A driven shaft defines a plurality of longitudinal slots and is coupled to the tool engaging chuck. The driven shaft is disposed within the chamber and has a longitudinal axis offset from the through axis. A plurality of vanes, each being partially formed of graphite, are individually disposed within one of the plurality of longitudinal slots.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 5 represents an exploded view of a driven shaft and associated vanes of the motor shown in FIG. 2;

Corresponding reference numerals indicate corresponding parts throughout the several views of the drawings.

DETAILED DESCRIPTION

Figure 1:
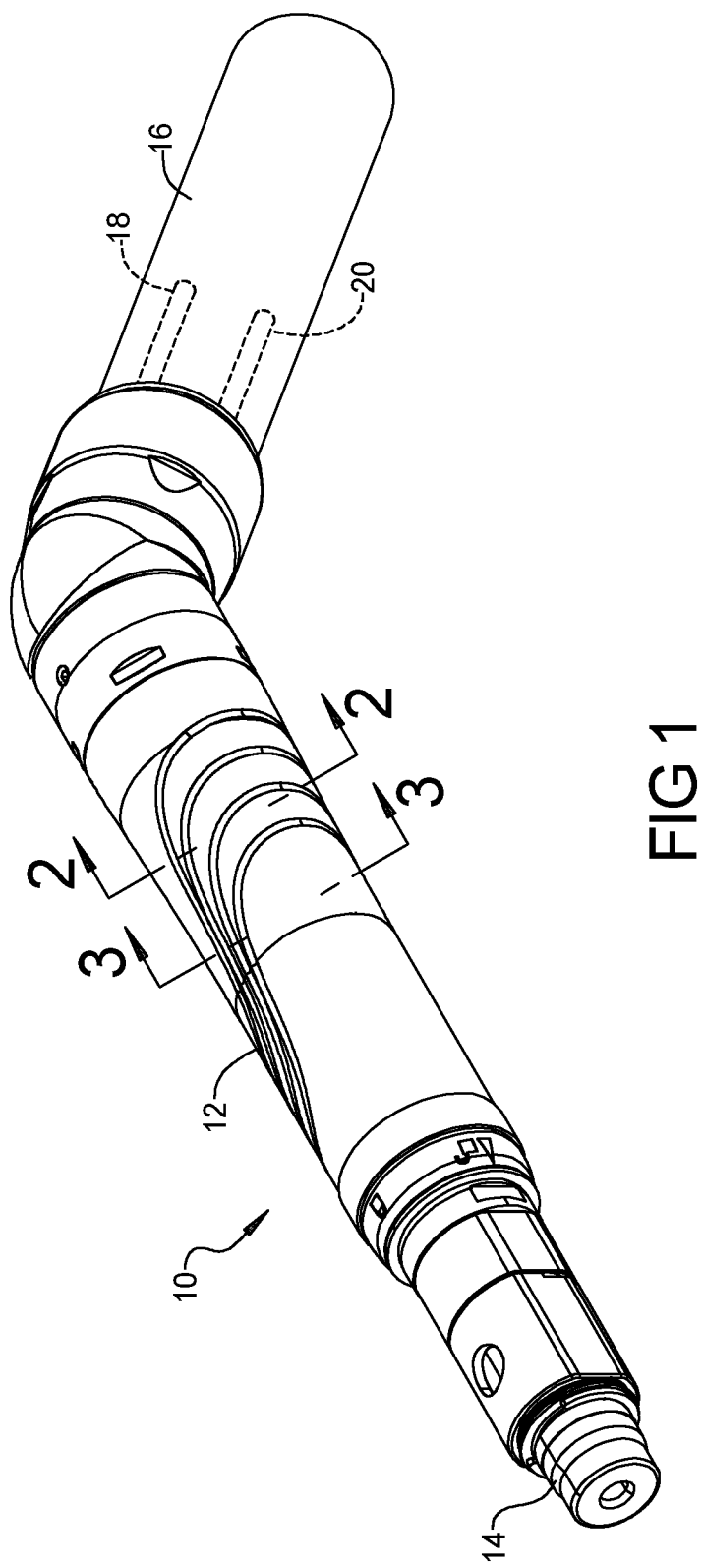
FIG. 1 represents a pneumatic drill according to the present teachings.

Example embodiments will now be described more fully with reference to the accompanying drawings. With reference to FIGS. 1 through 7D, shown is a pneumatic drill 10 according to the present teachings. FIG. 1 discloses a pneumatic drill 10 which has a pneumatic motor 12, tool engaging chuck 14, and a member or hose 16 carrying a high pressure air supply 18 and air exhaust 20. As is known, the tool engaging chuck 14 is configured to couple to a rotating tool such as a drill bit or cutting rasp.

Figure 2:
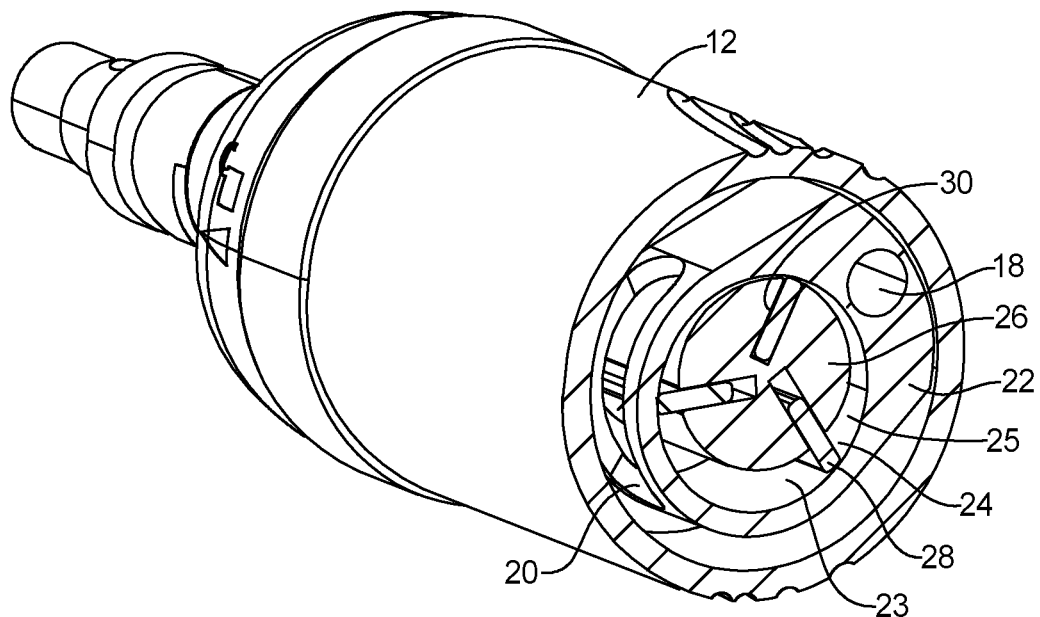
FIG. 2 represents a perspective sectional view of the pneumatic motor.
Figure 3A:
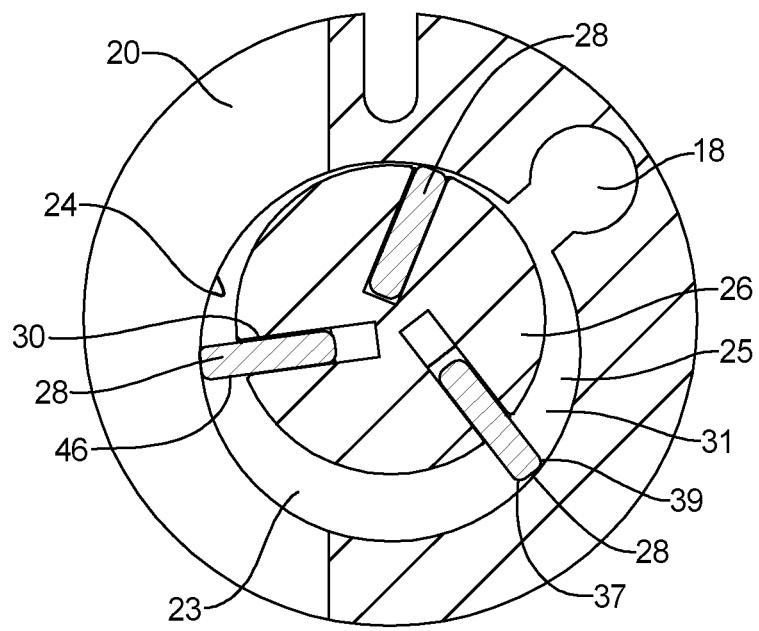
FIGS. 3A and 3B represent sectional views of the pneumatic motor shown in FIG. 2.
Figure 3B:
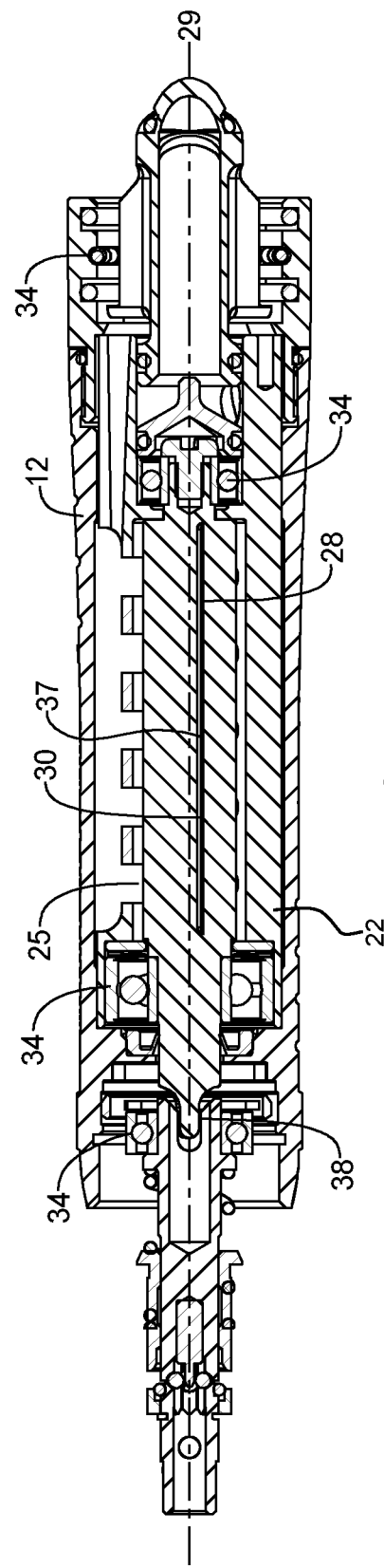

FIGS. 2, 3A and 3B represent a sectional view of the pneumatic motor 12. The pneumatic motor 12 has a housing 22 defining the high pressure air input 18 and an air output or exhaust 20, and defines an internal cylindrical chamber 23 having bearing surface 24 defining a through bore 25 along the longitudinal axis 27 of the motor. The motor 12 has a driven shaft 26 coupled to the tool engaging chuck 14. The driven shaft 26, which defines a plurality of longitudinal slots 30, is disposed within the cylindrical chamber 23 and has a longitudinal axis 29 offset from the housing chamber through axis 27. A plurality of vanes 28 being at least partially formed of graphite are individually and slidably disposed within one of the plurality of longitudinal slots 30.

The placement of the offset driven shaft 26 causes one of the vanes 28 to be longer than an adjacent vane 28 or extend radially outwardly from the shaft 26 a greater distance. This allows and provides for a larger area, which interacts with the high pressure gas, leading to the rotation of the driven shaft 26. As high pressure air comes in from the high-pressure supply 18 and into a chamber 31 defined by the driven shaft 26, the vanes 28 and housing 22, air pressure causes the rotation of the driven shaft 26, thus causing rotation of a tool held by the tool engaging chuck 14. Centrifugal forces from this rotation of the driven shaft 26 pulls all of the vanes 28 in a radial direction and positions a portion of each of the vanes 28 into engagement with the housing inner bearing surface 24, thus forming a bearing surface 37 for the high pressure. Each vane 28 has a bearing edge 39 slidably engaged against the bearing surface 24 that has at least partially exposed graphite to reduce the amount of friction between the vane 28 and a housing bearing surface 24. Alternatively, the bearing surface 24 can be formed by a graphite sleeve 24' inserted in the bore 25, as shown in FIG. 4B. The graphite sleeve can be 0.10 to 0.05 inches in thickness.

As the vanes 28 engage this bearing surface 24 or 24' and rotate along with the driven shaft 26, the vanes 28 define a plurality of separable chambers that allow for the flow of compressed air from the air supply 18, into the defined chamber 31, and after turning the shaft, out the exhaust port 20 similar to a paddle wheel. In one embodiment, three vanes 28 are radially disposed within the three equally spaced longitudinal slots 30 defined within the driven shaft 26 and slide within the slots 30 during rotation.

As shown, the driven shaft 26 defines three longitudinal slots 30. The first, second, and third vanes 28 have graphite, and are individually disposed within one of the three longitudinal slots 30. The first and second of the vanes, the housing, and the driven shaft define a high pressure compression chamber coupled to the high pressure air source. The second and third of the vanes 28, the housing, and the driven shaft 26 define a low pressure compression chamber which is fluidly couple to the exhaust port 20.

Figure 4A:
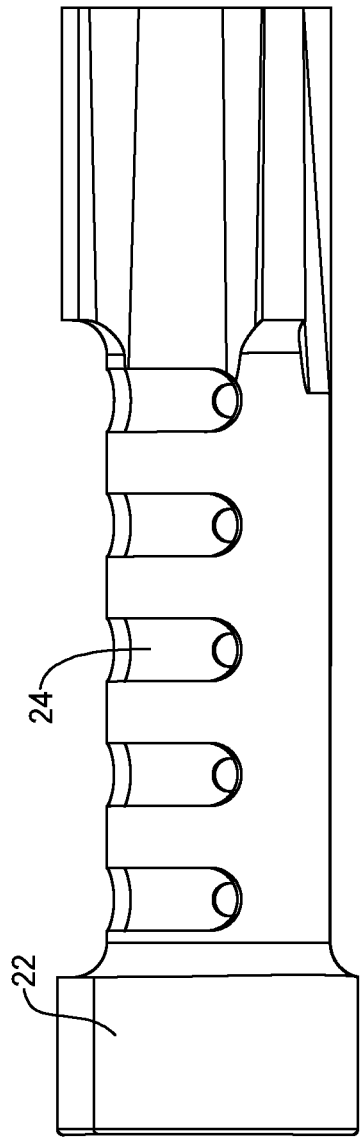
FIGS. 4A and 4B represent housing members for the pneumatic motor.
Figure 4B:
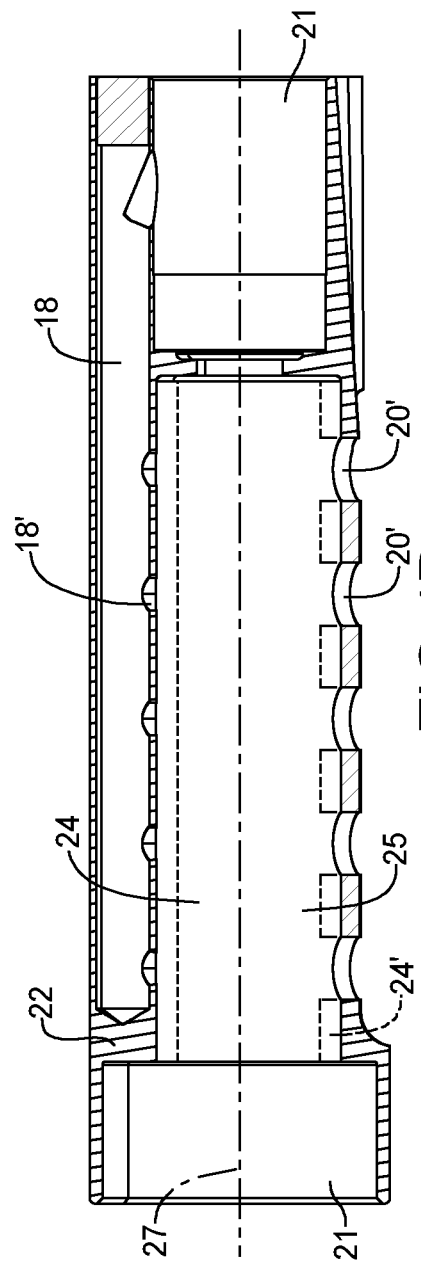

FIGS. 4A and 4B represent a housing member 22 that when disposed within the pneumatic motor 12 defines the high pressure input 18 and output air passages 20, and interior cylindrical bearing surfaces 24 which interact with the movable vane members 28. Defined in the wall of the cylindrical bearing surface is a plurality of input ports 18' that are fluidly coupled to the high-pressure air supply. Additionally defined within the wall of the cylindrical bearing surface 24 is a plurality of output ports 20' that allows for the passage of fluid within the chamber out of the pneumatic motor and into the output port 20'.

The housing 22 can be formed of stainless steel, or polymer. Optionally, the housing 22 and bearing surface 24 can each have graphite or other low friction material such as PTFE to reduce the friction between the moving vanes 28 and the bearing surface 24, such as the graphite sleeve 24', shown in FIG. 4B. In addition to the vane engaging surfaces, the housing 22 also defines a pair of inner surfaces 21 that support the bearings 34, that align the driven shaft 26 in a proper orientation within the cylindrical chamber and the input 18' and output 20' ports.

FIG. 5 represents an exploded view of a driven shaft 26 and associated vanes 28 of the motor shown in FIG. 2. The driven shaft 26 has at least one flat surface 38 that engages the tool-engaging member or chuck 14. Disposed toward the ends of the driven shaft 26 is a pair of cylindrical surfaces 42 that are conformed to couple to the bearings 34. The vanes 28 are slidably disposed within the slots 30 in a manner that allows the relative sliding of the vanes 28 within the slots 30 in a radial direction. In this regard, when the high pressure air is applied to the surface of the vanes 28, the driven shaft 26 is rotated, applying centrifugal forces onto the vanes 28, pulling them into engagement with the bearing surface 24 or 24' and exposing side surfaces which increase the effect of the compressed are on the vanes. As can be seen, as the driven shaft 26 is rotated, the vanes 28 are displaced by interaction with the bearing surface back into the slot 30.

Figure 6A:
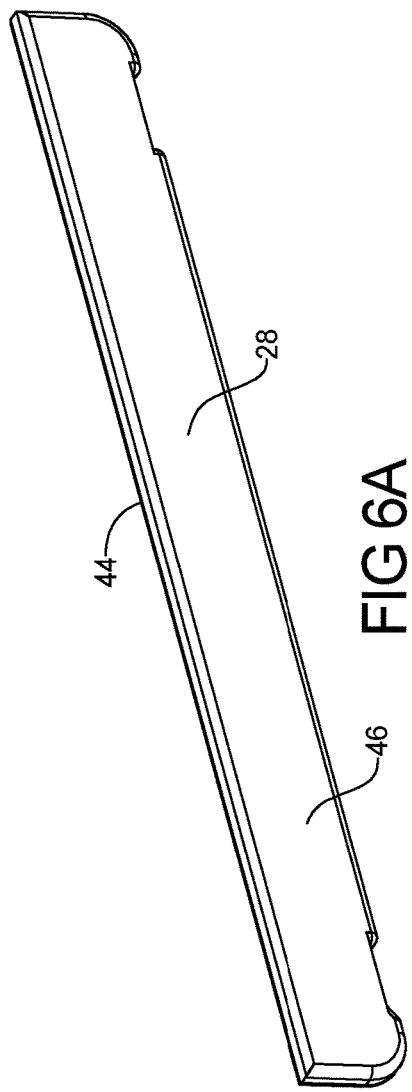
FIGS. 6A-6D represent graphite containing vanes according to the present teachings.
Figure 6C:
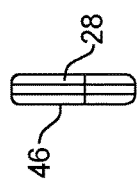
Figure 6B:
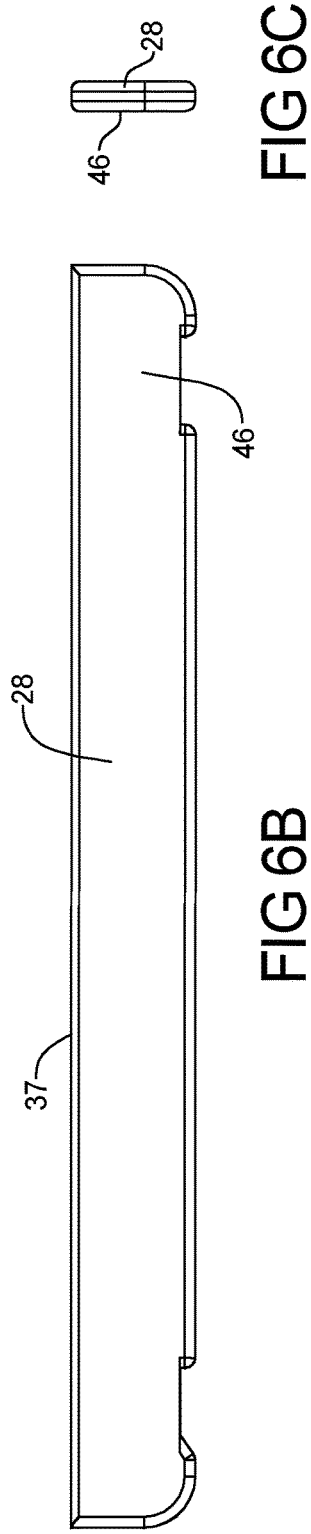
Figure 6D:
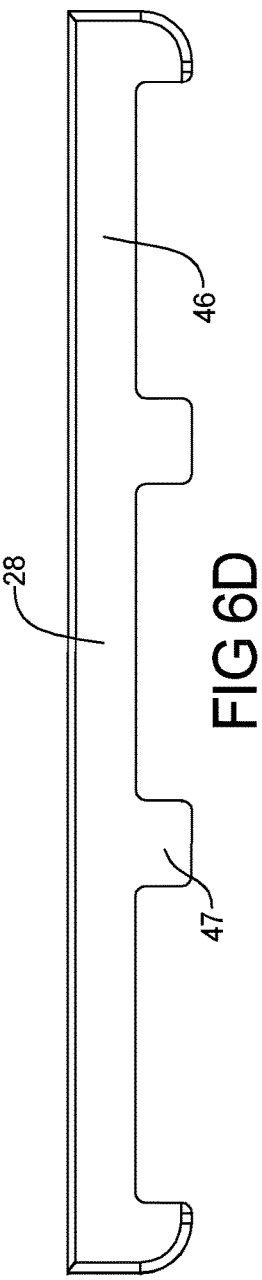

FIGS. 6-6D represent graphite containing vanes 28 according to the present teachings. These vanes 28 are preferably formed with graphite lubricant material. Because of the sensitivity of graphite to impact induced fracture, the vanes 28 are preferably formed of composite materials that incorporate graphite. In this regard, the vanes can be formed of a polymer such as PEEK with graphite in various forms which each have different properties. The vanes 28 have a first edge 44, which interfaces against the cylindrical bearing surface. The edge 44 has a surface that has exposed graphite that interfaces with the housing bearing surface. Additionally, the sides 46 of the vanes 28 interface with the metal slots 30 formed within the driven shaft 26. To reduce the weight of the vanes 28 and the frictional interaction with the slots 30, the vanes can have a plurality of offstanding flanges 47. The edges of the vanes 28 can be beveled to reduce the interaction of the vanes 28 with the slots.

The vanes 28, which are generally planar in configuration, have a top-bearing surface 44 that as described engages the interior bearing surface of the housing. The planar sides of the vanes 28, engage the sides 46 within the slots 30. To reduce friction, these planar sides 46 preferably have incorporated graphite which assist in the relative movement of the vanes 46 with respect to the rotatable shaft 26.

Figure 7A:
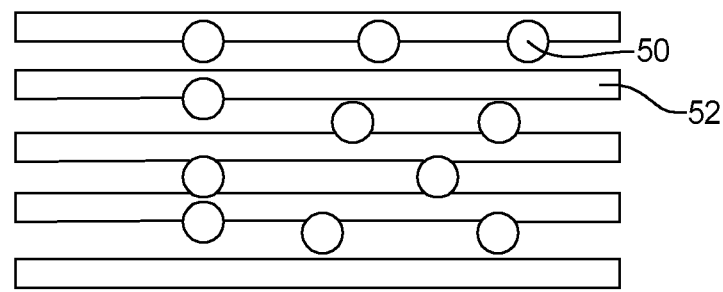
FIGS. 7A-7D represent material constructions of the vanes shown in FIGS. 6A-6D.
Figure 7B:
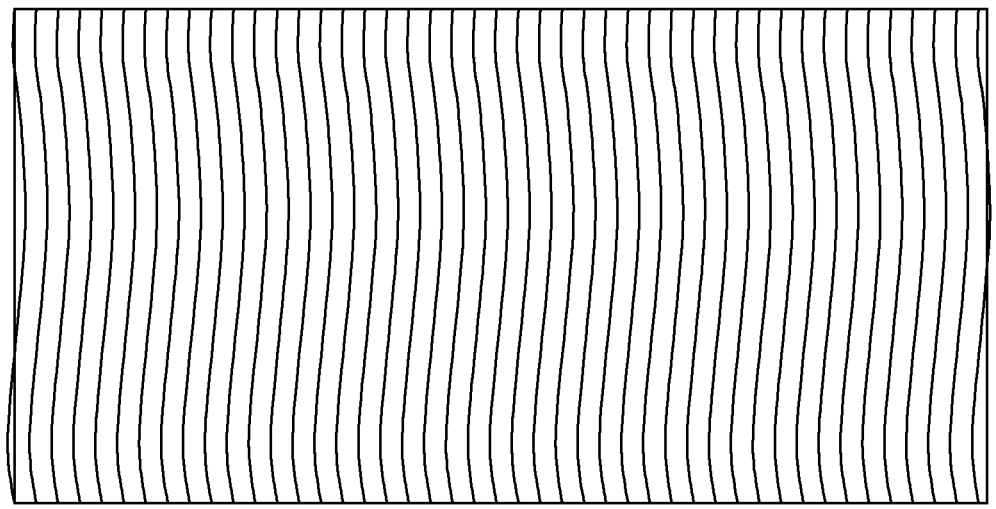
Figure 7C:
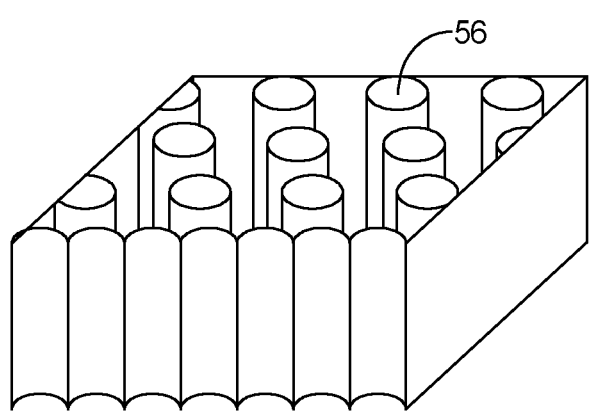

FIGS. 7A-7D represent material construction of the vanes shown in FIGS. 6A-6D. As shown in FIGS. 7A and 7B, the vanes can be formed of graphite containing composites. In one form, as shown in FIGS. 7A and 7B, the graphite material can be in the form of a powder 50, incorporated into a polymer matrix 52. This can occur by providing layers of polymer 52 and having graphite powder 50 incorporated there between. Additionally, the polymer can have a specific volume fraction of graphite powder incorporated into a liquid melt polymer. In this regard, the powder can be of a diameter from about 1000 nm to 100,000 nm, and can have a volume fraction from 10% graphite to about 90% graphite.

As shown in FIG. 7B, the composite material can be formed of alternating layers of graphite and polymer matrix such as PEEK. These layers can be parallel or perpendicular to the longitudinal axis of the shaft 26. In this configuration, the laminate can be formed such that the material layers within the vane 28 are visible along the bearing edge 39 of the vane 28, thus exposing the graphite material to the cylindrical bearing surface.

According to another embodiment, the graphite can be in tubular or fiber form 56. In this regard, the material can have fibers aligned either in the longitudinal direction of the driven shaft, or perpendicular to the cylindrical bearing wall. As the vane 28 wears, graphite is exposed, thus functioning as a dry lubricant between the moving vane and the bearing surface. Abrasion and wear materials are transferred out of the pneumatic motor through the exhaust port 20.

Figure 7D:
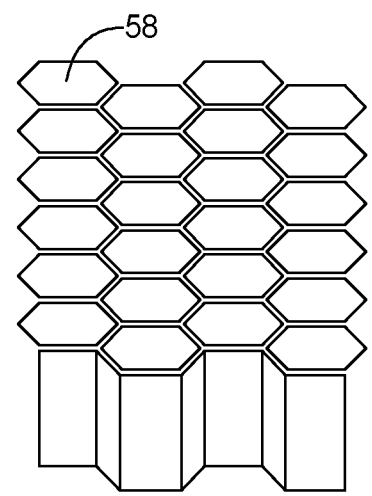

As shown in FIG. 7D, the material of the vanes can be a graphite honeycomb 58, having polymer matrix defining the honeycomb structure. Upon wear of the vane, the graphite is exposed, thus reducing friction at the vane to cylinder interface.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

The invention claimed is:

1. A surgical oil-less pneumatic drill comprising:
a tool engaging chuck;
a pneumatic motor, the tool engaging chuck and the pneumatic motor being disposed along a first longitudinal axis; and
a hose, the tool engaging chuck coupled to the pneumatic motor at one axial end of the pneumatic motor and the hose coupled to the pneumatic motor at the other opposing end of the pneumatic motor, the hose extending outwardly away from the pneumatic motor in a non-axial direction, the hose further including an air supply and an air exhaust;
the pneumatic motor having:
an air input and an air output, the air input in fluid communication with the air supply and the air output in communication with the air exhaust;
a housing defining an internal cylindrical chamber;
a graphite sleeve positioned within the internal cylindrical chamber having an inner bearing surface;
a driven shaft coupled to the tool engaging chuck, said driven shaft defining a plurality of longitudinal slots, said driven shaft being disposed within the cylindrical chamber and having a second longitudinal axis offset from the first longitudinal axis; and
a plurality of vanes comprising graphite, each of the plurality of vanes extending longitudinally from a first end to a second end and respectively disposed within one of the plurality of longitudinal slots;
wherein two of the vanes, the housing, the graphite sleeve, and the driven shaft define a compression chamber;
wherein each vane of the plurality of vanes has a bearing edge extending between the first end and the second end that is slidably engaged against the inner bearing surface of the graphite sleeve;
wherein each vane is respectively slidably disposed within the plurality of longitudinal slots, each vane having the first end having a first edge and the second end having a second edge, the bearing edge, first edge, and second edge are each beveled and the first and second ends each have rounded corners that are respectively disposed within the plurality of longitudinal slots; and
wherein each vane has a slot receiving edge opposed from the bearing edge where the opposed slot receiving edge includes a first off standing flange at the first end and a second off standing flange at the second end and a plurality of off standing flanges extending between the first and second off standing flanges.

2. The surgical oil-less pneumatic drill according to claim 1, wherein each vane has a composite structure.

3. The surgical oil-less pneumatic drill according to claim 2, wherein the composite structure is laminar.

4. The surgical oil-less pneumatic drill according to claim 2, wherein the composite structure comprises graphite particles disposed in a PEEK matrix.

5. The surgical oil-less pneumatic drill according to claim 1, wherein the plurality of vanes comprises three vanes radially disposed within three longitudinal slots defined within the driven shaft.

6. The surgical oil-less pneumatic drill according to claim 5, wherein each of the vanes has a pair of planar side bearing surfaces having graphite configured to engage first and second sides of the slots.

7. The surgical oil-less pneumatic drill according to claim 1, wherein each vane further being formed of at least one layer of layered material, each at least one layer of layered material comprising a layer of polymer material on to which a plurality of powdered graphite balls are deposited, each deposited powdered graphite ball has a non-contacting relationship with every other deposited powdered graphite ball on the layer of polymer material, and the at least one layer of layered material is arranged in each vane of the plurality of vanes so as to extend to each vane's bearing edge in a manner so that the bearing edge's portion of the at least one layer of layered material directly slidably engages against the inner bearing surface of the graphite sleeve.

8. The surgical oil-less pneumatic drill according to claim 1, wherein each powdered graphite ball has a diameter in the range from 1,000 nanometers to 100,000 nanometers.

9. The surgical oil-less pneumatic drill according to claim 1, wherein the driven shaft has an end that includes one flat surface, the one flat surface being received by the tool engaging chuck so as to be rotatably coupled to the tool engaging chuck, the housing including a bearing being disposed radially outbound from both the at least one flat surface and the tool engaging chuck, the bearing being adjacently engaged to the tool engaging chuck.

10. A surgical oil-less pneumatic drill comprising:
a pneumatic motor having:
a housing defining an internal cylindrical chamber having a through axis and defining an air input and an air output;
a graphite sleeve positioned within the internal cylindrical chamber of the housing having an inner bearing surface;
a driven shaft defining a plurality of longitudinal slots evenly spaced about a circumference of the driven shaft, said driven shaft being disposed within the chamber and having a longitudinal axis offset from the through axis; and
a plurality of vanes, each vane extending longitudinally from a first end to a second end and comprising graphite, each vane respectively disposed within one of the plurality of longitudinal slots;
wherein two of the vanes, the housing, the graphite sleeve, and the driven shaft define a compressed gas receiving chamber;
wherein each vane of the plurality of vanes has a bearing edge extending between the first end and the second end that is slidably engaged against the inner bearing surface of the graphite sleeve;
wherein each vane is respectively slidably disposed within the plurality of longitudinal slots, each vane having the first end having a first edge and the second end having a second edge, the bearing edge, first edge, and second edge are each beveled and the first and second ends each having rounded corners that are respectively disposed within the plurality of longitudinal slots; and
wherein each vane has a slot receiving edge opposed from the bearing edge, where the opposed slot receiving edge includes a first off standing flange at the first end and a second off standing flange at the second end and a plurality of off standing flanges extending between the first and second off standing flanges.

11. The surgical oil-less pneumatic drill according to claim 10, wherein each vane has one of a laminar and honeycomb composite structure.

12. The surgical oil-less pneumatic drill according to claim 11, wherein the composite structure comprises graphite particles disposed in a peek matrix.

13. The surgical oil-less pneumatic drill according to claim 10, wherein the plurality of vanes comprises three vanes radially disposed within three longitudinal slots defined within the shaft.

14. The surgical oil-less pneumatic drill according to claim 13, wherein each vane has a pair of planar side bearing surfaces having graphite configured to engage first and second sides of the slots.

15. A surgical oil-less pneumatic drill comprising:
a pneumatic motor having:
a housing defining an internal cylindrical chamber having a through axis;
a graphite sleeve positioned within the internal cylindrical chamber of the housing having an inner bearing surface;
a driven shaft defining a plurality of longitudinal slots, said driven shaft being disposed within the cylindrical chamber and having a longitudinal axis offset from the through axis; and
a plurality of vanes comprising graphite, each vane respectively disposed within the plurality of longitudinal slots;
wherein two of the vanes, the housing, the graphite sleeve, and the driven shaft define a high pressure compression chamber and two of the vanes, the housing, the graphite sleeve, and the driven shaft define a low pressure compression chamber;
wherein each vane extends longitudinally from a first end to a second end and each vane has a bearing edge that is slidably engaged against the inner bearing surface of the graphite sleeve and extending between the first end and the second end;
wherein each vane is respectively slidably disposed within the plurality of the longitudinal slots, each vane having the first end having a first edge and the second end having a second edge, the bearing edge, first edge, and second edge are each beveled and the first and second ends each have rounded corners that are respectively disposed within the plurality of longitudinal slots; and
wherein each vane has a slot receiving edge opposed from the bearing edge where the opposed slot receiving edge includes a first off standing flange at the first end and a second off standing flange at the second end and a plurality of off standing flanges extending between the first and second off standing flanges.

16. The surgical oil-less pneumatic drill according to claim 15, wherein each vane has the bearing edge comprising graphite slidably engaged against the bearing surface of the graphite sleeve.

17. The surgical oil-less pneumatic drill according to claim 15, wherein each of the vanes has a pair of planar side bearing surfaces having graphite configured to engage first and second sides of the slots.

18. The surgical oil-less pneumatic drill according to claim 15, wherein each vane comprises graphite particles disposed in a PEEK matrix.

* * * * *

UNITED STATES PATENT AND TRADEMARK OFFICE
CERTIFICATE OF CORRECTION

PATENT NO. : 11,072,028 B2
APPLICATION NO. : 15/907583
DATED : July 27, 2021
INVENTOR(S) : Md Zahedul Huq It is certified that error appears in the above-identified patent and that said Letters Patent is hereby corrected as shown below:

In the Specification

Column 3, Line 62, delete "FIGS. 6-6D" and insert --FIGS. 6A-6D-- therefor

Column 4, Line 18, delete "46" and insert --28-- therefor

In the Claims

Column 8, Line 39, In Claim 15, before "longitudinal", delete "the"

Signed and Sealed this
Thirty-first Day of May, 2022

Katherine Kelly Vidal
*Director of the United States Patent and Trademark Office*